United States Patent
Kato et al.

(10) Patent No.: US 12,168,064 B2
(45) Date of Patent: Dec. 17, 2024

(54) AQUEOUS DISPERSION OF A BLACK IRON OXIDE AND A LIQUID COSMETIC COMPRISING THE SAME

(71) Applicants: JO COSMETICS CO., LTD., Tokyo (JP); NISSIN CHEMICAL INDUSTRY CO., LTD., Echizen (JP)

(72) Inventors: Shogo Kato, Tokyo (JP); Kentaro Watanabe, Echizen (JP)

(73) Assignees: JO COSMETICS CO., LTD., Tokyo (JP); NISSIN CHEMICAL INDUSTRY CO., LTD., Echizen (JP)

(*) Notice: Subject to any disclaimer, the term of this patent is extended or adjusted under 35 U.S.C. 154(b) by 644 days.

(21) Appl. No.: 17/430,970

(22) PCT Filed: Feb. 12, 2020

(86) PCT No.: PCT/JP2020/005215
§ 371 (c)(1),
(2) Date: Aug. 13, 2021

(87) PCT Pub. No.: WO2020/166576
PCT Pub. Date: Aug. 20, 2020

(65) Prior Publication Data
US 2022/0133605 A1 May 5, 2022

(30) Foreign Application Priority Data
Feb. 15, 2019 (JP) ................. 2019-025622

(51) Int. Cl.
| | | |
|---|---|---|
| *A61K 8/19* | (2006.01) | |
| *A61K 8/04* | (2006.01) | |
| *A61K 8/58* | (2006.01) | |
| *A61K 8/73* | (2006.01) | |
| *A61Q 1/10* | (2006.01) | |

(52) U.S. Cl.
CPC .................. *A61K 8/19* (2013.01); *A61K 8/04* (2013.01); *A61K 8/585* (2013.01); *A61K 8/731* (2013.01); *A61Q 1/10* (2013.01); *A61K 2800/43* (2013.01); *A61K 2800/95* (2013.01)

(58) Field of Classification Search
CPC . A61K 8/19; A61K 8/04; A61K 8/585; A61K 8/731; A61K 2800/43; A61K 2800/95; A61K 2800/612; A61K 8/0241; A61K 2800/52; A61Q 1/10
See application file for complete search history.

(56) References Cited

U.S. PATENT DOCUMENTS

2014/0322281 A1  10/2014  Satou

FOREIGN PATENT DOCUMENTS

| JP | 2000-327948 A | 11/2000 |
|---|---|---|
| JP | 2004-244334 A | 9/2004 |
| JP | 2005-330222 A | 12/2005 |
| JP | 2006-232674 A | 9/2006 |
| JP | 2008-266503 A | 11/2008 |
| JP | 2012-184181 A | 9/2012 |
| JP | 2014-214103 A | 11/2014 |

OTHER PUBLICATIONS

International Search Report for PCT/JP2020/005215 mailed on Apr. 28, 2020.
Written Opinion of the International Searching Authority for PCT/JP2020/005215 (PCT/ISA/237) mailed on Apr. 28, 2020.

*Primary Examiner* — Robert A Wax
*Assistant Examiner* — Quanglong N Truong
(74) *Attorney, Agent, or Firm* — Birch, Stewart, Kolasch & Birch, LLP

(57) ABSTRACT

One of the purposes of the present invention is to provide an aqueous dispersion for cosmetics comprising black iron oxide, which has excellent dispersion stability, scarcely causes clogging to a pen type container for a long period of time, achieves good color development as a liquid cosmetic, and is capable of imparting the resulting film with water resistance. The other purpose of the present invention is to provide a liquid cosmetic comprising the aqueous dispersion. The present invention provides an aqueous dispersion comprising a black iron oxide, water and hydroxypropylmethyl cellulose phthalate, wherein the black iron oxide is surface-silylated with an alkyltriethoxysilane. The present invention further provides a method for preparing an aqueous dispersion containing the black iron oxide having a surface-silylated with an alkyltriethoxysilane.

16 Claims, No Drawings

AQUEOUS DISPERSION OF A BLACK IRON OXIDE AND A LIQUID COSMETIC COMPRISING THE SAME

TECHNICAL FIELD

The present invention relates to an aqueous dispersion of a black iron oxide for cosmetics and a liquid cosmetic comprising the aqueous dispersion. It particular, the present aqueous dispersion is suitable to be incorporated in cosmetics which are put in a pen type of container.

BACKGROUND ART

Typical black pigments for cosmetics are carbon black and black iron oxide. Carbon black is a black pigment excellent in color development to provide deep black color even in a small amount. However, some countries prohibit use of carbon black. On the other hand, black iron oxide is used throughout the world, because it has no problem in safety, but it has a problem in dispersibility.

Black iron oxide has difficulty in dispersibility, because black iron oxide has strong magnetism and, further, a large specific gravity. Even if it can be dispersed once, many coarse particles remain in the dispersion and are likely to precipitate and solidify with time. Therefore, where a cosmetic comprising black iron oxide is put into a pen-type container, black iron oxide is likely to cause clogging with time.

Various proposals have been made to overcome the above-described problems. For example, Patent Literature 1 describes a dispersion of pigment for cosmetics comprising black iron oxide in combination with red iron oxide and/or yellow oxide and an anionic dispersant. Aggregation caused by the magnetism of black iron oxide is avoided in such a dispersion, but its dispersion stability is insufficient and its color is brownish, not black. Patent Literature 2 describes a dispersion comprising a mixture of black iron oxide with red iron oxide, and a dispersant consisting of an α-olefin sulfonate and sodium sulfate. This dispersant is composed of low-molecular-weight surfactants which may cause irritation in eyes, so that the dispersant is unsuitable for use in eye makeups.

For example, Patent Literature 3 discloses a liquid cosmetic comprising a nonionic or anionic surfactant and an alcoholic solvent for stably dispersing black iron oxide in water. The liquid cosmetic is however inferior in water resistance (water repellency) and, therefore, has a defect that it comes off by sweat when it is, for instance, an eye makeup.

PRIOR LITERATURES

Patent Literatures

Patent Literature 1: Japanese Patent Application Laid-Open No. 2005-330222
Patent Literature 2: Japanese Patent Application Laid-Open No. 2012-184181
Patent Literature 3: Japanese Patent Application Laid-Open No. 2014-214103

SUMMARY OF THE INVENTION

Problems to be Solved by the Invention

As described above, there is a demand for an aqueous dispersion which comprises black iron oxide, does not cause clogging for a long period of time when a cosmetic comprising it, such as an eyeliner, is put into a pen-type container, and is capable of imparting water resistance to a cosmetic. One of the purposes of the present invention is to provide an aqueous dispersion for cosmetics, which dispersion comprises black iron oxide and has excellent dispersion stability, and a liquid cosmetic comprising the dispersion, contained in a pen-type container scarcely causes clogging for a long period of time, achieves good color development, and is capable of imparting the resulting film with water resistance. The other purpose of the present invention is to provide a liquid cosmetic comprising the aqueous dispersion.

Means for Solving the Problems

The present inventor conducted keen researches to solve the aforesaid problems and have found that an aqueous dispersion which has excellent dispersion stability so as not to cause aggregation for a long period of time and gives a film having good water resistance is obtained by silylating a black iron oxide with an alkyltriethoxysilane to obtain a surface-silylated black iron oxide and incorporating hydroxypropylmethyl cellulose phthalate as a dispersant in an aqueous dispersion of the black iron oxide.

That is, the present invention provides an aqueous dispersion comprising a black iron oxide, water and hydroxypropylmethyl cellulose phthalate, wherein the black iron oxide is surface-silylated with an alkyltriethoxysilane. The present invention further provides a method for preparing an aqueous dispersion comprising the black iron oxide surface-silylated with an alkyltriethoxysilane.

The aqueous dispersion of the present invention is excellent in dispersion stability, scarcely causes clogging in a pen-type container for a long period of time, and provides liquid cosmetic having good water resistance. In particular, an eyeliner comprising the dispersion has good water resistance and is excellent in color development.

DETAILED DESCRIPTION OF THE INVENTION

The present invention relates to an aqueous dispersion of a black iron oxide and a method for preparing the same. One of the characteristics of the aqueous dispersion is that a surface of the black iron oxide is silylated with alkyltriethoxysilane. The surface silylation of the black iron oxide suppresses aggregation of the black iron oxide to provide an aqueous dispersion having long-term stability. Further, the method for preparing an aqueous dispersion comprising the surface-silylated black iron oxide is characterized in that hydroxypropylmethyl cellulose phthalate is incorporated as a dispersant in the aqueous dispersion.

Hydroxypropylmethyl cellulose phthalate functions effectively to disperse the black iron oxide in water. Hydroxypropylmethyl cellulose phthalate is neutralized with an acid such as citric acid after the silylation reaction. The aqueous dispersion thus treated has improved water repellency, so that a liquid cosmetic containing the aqueous dispersion forms a coating film having good water resistance or water repellency. Further, the liquid cosmetic containing the hydroxypropylmethyl cellulose phthalate can be easily removed with soap.

The black iron oxide in the present invention is triiron tetraoxide ($Fe_3O_4$) and may be any known black pigment. The black iron oxide is preferably in the form of fine particle and may have an average primary particle size of from 0.01 to 1.0 μm, preferably from 0.05 to 0.5 μm, more preferably from 0.07 to 0.2 μm, in view of color development. In the present invention, the average primary particle size may be a number average particle size of 100 samples particles observed by a scanning electron microscope. The primary particle size of an individual particle is a diameter of a minimum circumcircle thereof. Shapes of the particles are not particularly limited as long as they have the aforesaid average particle size. Examples of the shape include spherical or approximately spherical, needle-like, spindle-like, plate-like, hexagonal plate-like, octahedral, and amorphous. They may be obtained, for example, according to the method described in Japanese Patent Application Laid-Open No. 2016-000763. Octahedral black iron oxide is preferable from the standpoint of a coloring power and blackness. The black iron oxide may contain inorganic elements other than iron or may be surface-coated with any inorganic compound other than iron compounds. In particular, the black iron oxide coated with an inorganic compound obtained by the method described in Japanese Patent Application Laid-Open No. 2016-000763 has a high blackness degree and is therefore preferable. The coating inorganic compound is preferably an oxide or hydroxide of aluminum or silicon. For the coated black iron oxide, the amount of the black iron oxide does not contain an amount of inorganic elements nor the coating inorganic compound.

The aqueous dispersion of the present invention contains the surface-silylated black iron oxide in an amount of 1 to 30 mass % as the black iron oxide. The amount of the black iron oxide does not include the amount of the silyl moiety present on the surface of the black iron oxide. The amount of the black iron oxide in the aqueous dispersion is from 1 to 30 mass %, preferably from 10 to 27 mass %, more preferably from 15 to 23 mass %, based on the total mass of the aqueous dispersion. The amount within this range ensures good dispersion stability.

The alkyltriethoxysilane is known as a silylating agent. The alkyl group may have 1 to 10 carbon atoms, preferably 1 to 5 carbon atoms. Examples of the alkyltriethoxysilane include methyltriethoxysilane and ethyltriethoxysilane. The alkyltriethoxysilane is highly reactive with the black iron oxide and the by-produced ethanol is safe and easily distilled off. Therefore, the alkyltriethoxysilane is easy to handle as a silylating agent for the black iron oxide and is preferred.

The amount of the alkyltriethoxysilane used for the silylation may be from 0.5 to 20 parts by mass, preferably from 1 to 15 parts by mass, more preferably from 3 to 10 parts by mass, relative to 100 parts by mass of the black iron oxide. By silylating the surface of the black iron oxide in an amount of the aforesaid range, aggregation of the black iron oxide is effectively suppressed and an aqueous dispersion having long-term stability is provided. If the amount of the alkyltriethoxysilane is less than the aforesaid lower limit, the aforesaid effects are not attained sufficiently. If the amount of the alkyltriethoxysilane is larger than the aforesaid upper limit, aggregation of the particles may occur, so that color development of a cosmetic may be poor. Almost all of the alkyltriethoxysilane in an amount within the aforesaid range adheres to the surface of the black iron oxide in the silylation. However, the aqueous dispersion of the present invention may contain a free alkyltriethoxysilane without participating in the silylation. In the aqueous dispersion of the present invention, therefore, the amount of the alkyltriethoxysilane may be from 0.5 to 20 parts by mass, preferably from 1 to 15 parts by mass, more preferably from 3 to 10 parts by mass, relative to 100 parts by mass of the black iron oxide.

The viscosity of the hydroxypropylmethyl cellulose phthalate may be selected properly, preferably from 10 to 200 mPa·s, more preferably from 10 to 100 mPa·s, at 20° C. in a 1% aqueous solution. In the present invention, the viscosity of the hydroxypropylmethyl cellulose phthalate is determined by a B type viscosimeter. The hydroxypropylmethyl cellulose phthalate may be a commercially available product, such as HP-55, ex Shin-Etsu Chemical Co., Ltd.

The amount of the hydroxypropylmethyl cellulose phthalate in the aqueous dispersion is preferably from 0.1 to 10 parts by mass, more preferably from 0.2 to 5 parts by mass, relative to 100 parts by mass of the black iron oxide. If the amount is less than the aforesaid lower limit, the dispersibility of the aqueous dispersion may be worse markedly, which is not preferred. If the amount is larger than the aforesaid upper limit, the viscosity of the aqueous dispersion may be significantly large, so that an eyeliner cannot come out from a container.

Hydroxypropylmethyl cellulose acetate succinate may be used in combination with the hydroxypropylmethyl cellulose phthalate. A total amount of hydroxypropylmethyl cellulose acetate succinate and hydroxypropylmethyl cellulose phthalate is preferably 0.1 to 10 parts by mass, per 100 parts by mass of the black iron oxide. The hydroxypropylmethyl cellulose acetate succinate preferably has a viscosity at 20° C. of from 1 to 200 mPa·s. For example, a commercially available product, Shin-Etsu AQOAT (ex Shin-Etsu Chemical Co., Ltd.) is usable.

The method for preparing the aqueous dispersion will be described below in detail.

The aqueous dispersion of the black iron oxide according to the present invention is obtained by a silylation of the black iron oxide with the alkyltriethoxysilane in the presence of hydroxypropylmethyl cellulose phthalate in water. A pH of the reaction mixture is preferably basic. Sodium carbonate may be added to make a pH of the reaction mixture basic. For the reaction, an alkali catalyst is preferably added. Specifically, while stirring hydroxypropylmethyl cellulose phthalate and the black iron oxide in an ammonia solution with a stirrer such as homogenizer, an alkyltriethoxysilane is added dropwise to cause silylation of the black iron oxide and to disperse the pigment in water. The reaction temperature may be adjusted properly and is preferably from room temperature to 80° C. Next, ammonia and a byproduct, ethanol, are distilled off, and the residue is neutralized with an acid such as citric acid to obtain an aqueous dispersion. The aqueous dispersion thus obtained preferably has a pH of from 6 to 8. If necessary, a step of breaking up aggregates with a wet pulverization device (e.g., Star Burst) may be carried out. An antiseptic or an antibiotic may be added to the aqueous dispersion thus obtained, if necessary.

The dispersion medium in the present aqueous dispersion is preferably water such as ion-exchanged water, purified water, distilled water and pure water and may contain an organic solvent if necessary. The surface of the black iron oxide obtained by the present preparation method is silylated and thereby hydrophobized and, therefore, aggregation of the black iron oxide is suppressed and dispersion stability in water improves. The silylation of the surface of the black iron oxide can be confirmed, for example, by a fact that a coating obtained has improved water repellency. The silylation can also be confirmed by observing the surface structure with a scanning electron microscope (SEM) or a transmission electron microscope (TEM).

An embodiment of the method for preparing the present aqueous dispersion will be described below.

First, hydroxypropylmethyl cellulose phthalate and ion-exchanged water are mixed to prepare an aqueous solution. Here, sodium carbonate may be added to make the pH basic. Next, the resulting aqueous solution is added to ion-exchanged water and, while stirring with a homomixer, black iron oxide and, if necessary, further ion-exchanged water are added. At this time, aqueous ammonia is preferably added as an alkali catalyst. The alkyltriethoxysilane is added dropwise while stirring to cause silylation. Then, water comprising ammonia and ethanol is distilled off, the pH of the residue is adjusted and, if necessary, a step of breaking-up with a wet pulverization device (e.g., Star Burst) is conducted to obtain the aqueous dispersion.

The present invention also provides a liquid cosmetic comprising the aqueous dispersion. The amount of the aqueous dispersion of the present invention in the liquid cosmetic is preferably from 0.1 to 40 mass %, more preferably from 2 to 20 mass %, as the amount of the black iron oxide, based on the amount of the cosmetic. On account of the incorporation of the aqueous dispersion in the aforesaid range, the liquid cosmetic has excellent long-term storage stability and gives a coating film having excellent water repellency. If the amount of the aqueous dispersion is less than the aforesaid lower limit, color development is poor and a liquid cosmetic is unsatisfactory. If the amount is larger than the aforesaid upper limit, the resulting cosmetic may have a too high viscosity, which is not preferred.

A film-forming polymer emulsion may be added to the liquid cosmetic of the present invention. The amount of the film-forming polymer emulsion is preferably from 1 to 30 mass % as a solid content (i.e., the amount of the film-forming polymer), based on the mass of the liquid cosmetic. By incorporating the film-forming polymer emulsion, the obtained liquid cosmetic such as an eye liner is excellent in water resistance and durability—so as to have make-up durable, for example, against sweat. Preferably, the amount of the film-forming polymer is from 2 to 25 mass %, more preferably from 5 to 20 mass %, relative to the amount of the liquid cosmetic. If the amount of the film-forming polymer is less than the aforesaid lower limit, the water resistance of the liquid cosmetic is not sufficient. If the amount is larger than the aforesaid upper limit, the viscosity of resulting liquid cosmetic is too high, so that when it is a line drawn by an eye liner contained in a pen-type container may be fuzzy.

The film-forming polymer emulsion to be used in the present invention may be any known one used in cosmetics. Examples of the film-forming polymer emulsion include alkyl acrylate copolymer emulsion, alkyl methacrylate copolymer emulsion, (styrene/alkyl acrylate)copolymer emulsion, (styrene/alkyl methacrylate)copolymer emulsion, vinyl acetate polymer emulsion, (vinylpyrrolidone/styrene) copolymer emulsion, (alkyl acrylate/vinyl acetate)copolymer emulsion, (alkyl methacrylate/vinyl acetate) copolymer emulsion, (acrylic acid/alkyl acrylate)copolymer emulsion, (acrylic acid/alkyl methacrylate) copolymer emulsion, (methacrylic acid/alkyl acrylate) copolymer emulsion, (methacrylic acid/alkyl methacrylate)copolymer emulsion, and (alkyl acrylate/dimethicone) copolymer emulsion.

Examples of the alkyl acrylate copolymer emulsions include those named ACLYLATES COPOLYMER in INCI (International Nomenclature Cosmetic Ingredient labeling names). Examples of the commercially available products thereof include YODOSOL GH800F (ex Akuzo Nobel). Examples of the (acrylic acid/alkyl acrylate)copolymer emulsion include polymers named ACLYLATES/ETHYLHEXYLACRYLATE COPOLYMER in INCI and DAITOSOL 5000SJ (ex Daito Kasei) is an example of the commercially available products thereof. Examples of the (styrene/alkyl methacrylate)copolymer emulsion include polymers named STYLENE/ACLYLATES COPOLYMER in INCI and DAITOSOL 5000STY (ex Daito Kasei) is an example of the commercially available product thereof. These polymer emulsions may be used singly or in combination thereof.

The liquid cosmetic of the present invention may further comprise other components as long as its performance is not detracted. Examples of the other components include pH neutralizing agents, antiseptics, and thickeners. Further, the liquid cosmetic may comprise a polyhydric alcohol as a solvent, powders other than the black iron oxide, and a dispersant other than hydroxypropylmethyl cellulose phthalate. Examples of the pH neutralizing agent include citric acid, ascorbic acid, sodium carbonate, and AMP (aminomethyl propanol). Examples of the antiseptic include phenoxyethanol, pentylene glycol, and ethanol. Examples of the thickener include carbomer, xanthan gum, and dextrin palmitate. The amount of them is not particularly limited and may be adjusted properly so that the effects of the present invention are not detracted.

The polyhydric alcohol is not particularly limited and may be any one used commonly in cosmetics. Examples of the polyhydric alcohol include propylene glycol, dipropylene glycol, 1,3-butylene glycol, 1,2-pentylene glycol, 3-methyl-1,3-butanediol, polyethylene glycol, glycerin, diglycerin, and tetraglycerin. These polyhydric alcohols may be used singly or two or more in combination. The amount of the polyhydric alcohol is preferably from 0.1 to 20 mass %, more preferably from 1 to 15 mass %, based on the total amount of the cosmetic. The liquid cosmetic comprising the polyhydric alcohol has improved antiseptic ability and drying at a pen tip or brush of a pen-type container is prevented.

The powders other than the black iron oxide are not particularly limited and may be any one used commonly in cosmetic. For example, they may have a shape and size, such as plate, spindle, or needle, or a particle structure such as porous or non-porous. Examples of the powder include inorganic powders, glitter powders, organic powders, pigment powders, and composite powders. More specific examples include inorganic powders such as Prussian blue, ultramarine, red oxide, yellow oxide, titanium oxide, zinc oxide, aluminum oxide, cerium oxide, silicic anhydride, magnesium oxide, zirconium oxide, magnesium carbonate, calcium carbonate, chromium oxide, chromium hydroxide, carbon black, aluminum silicate, magnesium silicate, magnesium aluminum silicate, mica, synthetic mica, synthetic sericite, sericite, talc, kaolin, silicon carbide, barium sulfate, bentonite, smectite, and boron nitride; glitter powders such as bismuth oxychloride, titanium mica, iron oxide-coated mica, iron oxide-coated titanium mica, silicic acid anhydride-coated titanium mica, organic pigment-treated titanium mica, titanium oxide-coated glass powders, titanium oxide/iron oxide-coated glass powders, titanium oxide/silicic acid anhydride-coated glass powders, and aluminum powders; organic powders such as magnesium stearate, zinc stearate, N-acyl-lysine, and nylon; pigment powders such as organic tar-based pigments and lake pigments which are organic pigments, composite powders such as fine-particle titanium oxide-coated titanium mica, fine-particle zinc oxide-coated titanium mica, barium sulfate-coated titanium mica, titanium oxide-containing silicon dioxide, and zinc oxide-containing silicon dioxide; polyethylene terephthalate/aluminum/epoxy laminated powders, polyethylene terephthalate/polyolefin laminated film powders, and polyethylene terephthalate/polymethyl methacrylate laminated film powders. They may be used alone or in combination thereof.

As a dispersant other than hydroxypropylmethyl cellulose phthalate, preferred is those used mainly for dispersing the aforesaid powders other than black iron oxide such as polyaspartic acid, polyacrylates, and water-soluble acrylic acid-based polymers and salts thereof.

The method for preparing the liquid cosmetic is not particularly limited and may be any known methods. For example, the aqueous dispersion of the present invention is put in a container and water (pure water or ion-exchanged water), a polyhydric alcohol (for example, glycol), a pH neutralizing agent, an antiseptic, a thickening agent and a film-forming agent are added with stirring by a known stirring means such as propeller type stirring device for a predetermined period of time. The stirring time may be set as desired, particularly stirring and mixing may be conducted for 30 minutes to 60 minutes.

The liquid cosmetic of the present invention may be put in a desired cosmetic container and used, for example, with a pen tip or a brush which is integrated with the container. The liquid cosmetic of the present invention preferably has a viscosity at 25° C. of from 1 to 300 mPa·s, more preferably from 1 to 100 mPa·s, still more preferably from 2 to 20 mPa·s. When the liquid cosmetic is contained in a pen-type container, its viscosity is preferably from 2 to 15 mPa·s, more preferably from 4 to 10 mPa·s. When the liquid cosmetic is an eyeliner contained in a pen-type container, a high viscosity of the liquid cosmetic is not preferred, because the liquid cosmetic does not come out from the pen tip. The viscosity of the liquid cosmetic may be determined by a tuning fork vibration viscometer, SV-100, ex A&D.

EXAMPLES

The present invention will be explained below in further detail with reference to a series of the Examples and the Comparative Examples, though the present invention is in no way limited by these Examples.

Example 1

Preparation of Aqueous Dispersion 1

1 Gram of hydroxypropylmethyl cellulose phthalate (ex Shin-Etsu Chemical Co., Ltd., trade name: HP-55), 1 g of sodium carbonate, and 98 g of ion-exchanged water were mixed to prepare a 1 mass % aqueous solution of HP-55 in advance. 62.5 Grams of an aqueous 1 mass % solution of HP-55 was added to 150 g of ion-exchanged water, to which 70.2 g of black iron oxide fine-particle (ex Titan Kogyo Co., trade name: ABL-412HP, $Fe_3O_4$: 98%, $Al(OH)_3$: 2%, average primary particle size: 0.1 µm), 53 g of ion-exchanged water, and 22.5 g of an aqueous 25% solution of ammonia were added, while stirring with a homomixer (number of revolutions: 5000 rpm). While stirring at 25° C., 9 g of methyltriethoxysilane was continuously added dropwise over 30 minutes to cause sylylation and aged at an elevated temperature of 60° C. for one hour. Then, 80 ml of water containing ammonia and ethanol was distilled off in vacuum, while keeping the temperature at 60 to 70° C., to obtain about 330 g of an aqueous dispersion. 50 Grams of ion-exchanged water was used for washing. The aggregates were broken up twice at 100 MPa with a Star Burst. 12 Grams of an aqueous 10 mass % solution of citric acid was added to adjust the pH of the dispersion to 6.0 to 8.0 and, then, 3.3 g of phenoxyethanol and 13.2 g of pentylene glycol were added. Thus obtained was aqueous dispersion 1 having a solid content of about 21 mass % (black iron oxide content: about 19 mass %). The aqueous dispersion 1 contained 0.2 mass % (as calculated) hydroxypropylmethyl cellulose phthalate. According to observation by TEM, it was confirmed that the surface of the black iron oxide was silylated.

Example 2

Preparation of Aqueous Dispersion 2

1 Gram of hydroxypropylmethyl cellulose phthalate (ex Shin-Etsu Chemical Co., Ltd., trade name: HP-55), 1 g of sodium carbonate, and 98 g of ion-exchanged water were mixed to prepare a 1 mass % aqueous solution of HP-55 in advance. 187.5 Grams of an aqueous 1 mass % solution of HP-55 was added to 20 g of ion-exchanged water, to which 70.2 g of black iron oxide fine-particle (ex Titan Kogyo, trade name: ABL-412HP), 53 g of ion-exchanged water, and 22.5 g of an aqueous 25% solution of ammonia were added, while stirring with a homomixer (number of revolutions: 5000 rpm). While stirring at 25° C., 9 g of methyltriethoxysilane was continuously added dropwise over 30 minutes to cause sylylation and aged at an elevated temperature of 60° C. for one hour. Then, 80 ml of water containing ammonia and ethanol was distilled off in vacuum, while keeping the temperature at 60 to 70° C., to obtain about 330 g of an aqueous dispersion. 50 Grams of ion-exchanged water was used for washing. 12 Grams of an aqueous 10 mass % solution of citric acid was added to adjust the pH of the dispersion to 6.0 to 8.0 and, then, 3.3 g of phenoxyethanol and 13.2 g of pentylene glycol were added. Thus obtained was aqueous dispersion 2 having a solid content of about 22 mass % (black iron oxide content: about 19 mass %). The aqueous dispersion 2 contained 0.5 mass % (as calculated) hydroxypropylmethyl cellulose phthalate.

Comparative Example 1

Preparation of Aqueous Dispersion 3

The procedures of Example 1 were repeated to obtain an aqueous dispersion 3, except that methyltriethoxysilane was not incorporated. The black iron oxide aggregated and precipitated just after the preparation, so that a uniform dispersion was not obtained.

Comparative Example 2

Preparation of Aqueous Dispersion 4

To 202 g of ion-exchanged water, 1.6 g of an aqueous solution of sodium polyaspartate (solid content: 38%), 70.2 g of black iron oxide fine-particle (ex Titan Kogyo, trade name: ABL-412HP) were added and stirred for one hour, while stirring with a homomixer (number of revolutions: 5000 rpm) to obtain about 330 g of an aqueous dispersion. 50 Grams of ion-exchanged water was used for washing. 6 Grams of an aqueous 10 mass % solution of citric acid was added to the resulting aqueous dispersion to neutralize the pH of the dispersion to 6.0 to 8.0, 3.3 g of phenoxyethanol and 13.2 g of pentylene glycol were added and thereto obtain an aqueous dispersion 4 having a solid content of about 21 mass % (black iron oxide content: about 20 mass %).

Comparative Example 3

Preparation of Aqueous Dispersion 5

1.6 Grams of an aqueous solution of sodium polyaspartate (solid content: 38%) was added to 210 g of ion-exchanged water, to which 70.2 g of black iron oxide fine-particle (ex Titan Kogyo, trade name: ABL-412HP), 53 g of ion-exchanged water, and 22.5 g of an aqueous 25% solution of ammonia were added, while stirring with a homomixer (number of revolutions: 5000 rpm). While stirring at 25° C., 9 g of methyltriethoxysilane was continuously added dropwise over 30 minutes to cause sylylation and aged at an elevated temperature of 60° C. for one hour. Then, 80 ml of water containing ammonia and ethanol was distilled off in vacuum, while keeping the temperature at 60 to 70° C., to obtain about 330 g of an aqueous dispersion. 50 Grams of ion-exchanged water was used for washing. 12 Grams of an aqueous 10 mass % solution of citric acid was added to adjust the pH of the dispersion to 6.0 to 8.0 and, then 3.3 g of phenoxyethanol and 13.2 g of pentylene glycol were added. Thus obtained was aqueous dispersion 5 having a solid content of about 21 mass % (black iron oxide content: about 19 mass %).

As described above, the aqueous dispersion 3 of Comparative Example 1 where the black iron oxide was not treated with methyltriethoxysilane and aggregated severely, so that the dispersion was unusable in a cosmetic. Therefore, the aqueous dispersion 3 was not subjected to the following evaluations.

Evaluation of Water Repellency (or Water Resistance) of a Film

The aqueous dispersions obtained in the Examples 1 and 2 and Comparative Examples 2 and 3 were each applied on a slide glass by a 2-mil bar coater, followed by drying at 25° C. for 2 hrs to form a film. 0.1 Microliter of water was dropped on the resulting film. Thirty seconds after, a contact angle was determined with an automatic contact angle meter, DCA-VZ, ex Kyowa Interface Science. The results are as shown in Table 1.

TABLE 1

| Part by mass | | Ex. 1 | Ex. 2 | Com. Ex. 2 | Com. Ex. 3 |
|---|---|---|---|---|---|
| Component of the aqueous dispersion, part by mass | a) Black iron oxide | 100 | 100 | 100 | 100 |
| | b) Hydroxypropylmethyl cellulose phthalate1 | 1.05 | 2.63 | — | — |
| | c) Methyltriethoxysilane | 13.1 | 13.1 | — | 13.1 |
| | Solution of sodium polyaspartate | — | — | 2.3 (0.87) | 2.3 (0.87) |
| Evaluation | Water repellency, water contact angle, | 126 | 71 | ≤10 | 139 |

As seen in Table 1, the aqueous dispersions of the present invention gave a film having good water repellency and, thus, good water resistance. The comparison between Example 1 and Example 2 shows that the water repellency (water resistance) of a film may be controlled by the amount of hydroxypropylmethyl cellulose phthalate.

Black-Color Development

Eyeliner compositions were prepared as shown in Table 2, comprising the aqueous dispersions of Examples 1 and 2 and Comparative Examples 2 and 3. Each of the eyeliner compositions was put into a pen-type container. The eyeliner composition was applied from the brush tip of the eyeliner container in a 2 cm$^2$ area on paper. Black-color development was evaluated by L* value of the film measured by a simple spectroscopic color difference meter (NF-333, ex Nippon Denshoku Industries). The results are as shown in Table 2. A preferred L* value is 42 or less.

The viscosity and pH of the eyeliner composition which is in a liquid state were determined at 25° C. The results are as shown in Table 2. The viscosity was determined by Tuning Fork Vibration Viscometer SV-100A, ex A&D.

TABLE 2

| Components of The eyeliner composition, part by mass | | Ex. 1 | Ex. 2 | Com. Ex. 2 | Com. Ex. 3 |
|---|---|---|---|---|---|
| Dispersion (iron oxide content in brackets) | Aqueous dispersion 1 | 45.0 (8.6) | | | |
| | Aqueous dispersion 2 | | 45.0 (8.6) | | |
| | Aqueous dispersion 4 | | | 45.0 (9.0) | |
| | Aqueous dispersion 5 | | | | 45.0 (8.6) |
| Solvent | Water | Balance | Balance | Balance | Balance |
| | Pentylene glycol | 3.0 | 3.0 | 3.0 | 3.0 |
| pH neutralizing agent | Aminomethyl propanol | 0.1 | 0.1 | 0.1 | 0.1 |
| Antiseptic | Paraben | 0.1 | 0.1 | 0.1 | 0.1 |
| | Phenoxyethanol | 0.5 | 0.5 | 0.5 | 0.5 |
| Thickening agent | Xanthan gum | 0.1 | 0.1 | 0.1 | 0.1 |
| Film-forming polymer emulsion (Resin content in the composition) | Acrylate Copolymer[X.1] | 25.0 (11.5) | 25.0 (11.5) | 25.0 (11.5) | 25.0 (11.5) |
| | Styrene Acrylate Copolymer[X.2] | 5.0 (2.5) | 5.0 (2.5) | 5.0 (2.5) | 5.0 (2.5) |
| Total amount | | 100 | 100 | 100 | 100 |
| Evaluation | Viscosity, mPa·s | 6.0 | 6.9 | 6.9 | 5.9 |
| | pH | 8.7 | 8.3 | 8.6 | 8.7 |
| | Black-color development, initial, L* value of the film | 39.8 | 36.2 | 45.3 | 50.6 |
| | Black color development after stored at 40° C. for one month L* value of the film | 41.6 | 35.5 | 47.8 | 49.1 |

[X.1]YODOSOL GH810F, solid content of 46%, ex Akzo Nobel
[X.2]DAITOSOL 5000STY, solid content of 50%, ex Daito Kasei Co.

As seen in Table 2, the eyeliner comprising aqueous dispersion 4 of Comparative Example 2 comprising, as a dispersant for black iron oxide, sodium polyaspartate showed the poor black-color development. The black-color development of the eyeliner after stored was further worse. This means that the eyeliner was inferior in dispersion stability. The eyeliner of Comparative 3 which was prepared with the aqueous dispersion of Comparative 2 and adding methyltriethoxysilane was also inferior in dispersion stability.

In contrast, as seen in Examples 1 and 2, the eyeliners comprising the aqueous dispersions of the present invention showed the good black-color development. The eyeliners did not draw a fuzzy line so that it came out smoothly from the container. The eyeliner was still capable of coming out smoothly from the container even after stored at 40° C. for one month. Thus, it is excellent in dispersion stability.

INDUSTRIAL APPLICABILITY

The aqueous dispersion of the present invention has excellent dispersion stability. The liquid cosmetic comprising the aqueous dispersion has good water resistance and scarcely causes clogging in a pen-type container for a long period of time. Therefore, the aqueous dispersion is particularly suited for use in an eyeliner having good water resistance.

The invention claimed is:

1. A liquid cosmetic comprising an aqueous dispersion comprising a black iron oxide, water and hydroxypropylmethyl cellulose phthalate, wherein the black iron oxide is surface-silylated with an alkyltriethoxysilane and an amount of the aqueous dispersion in the liquid cosmetic is such that the amount of the black iron oxide is 0.1 to 40 mass %, relative to the liquid cosmetic.

2. The liquid cosmetic according to claim 1, wherein the aqueous dispersion comprises the surface-silylated black iron oxide in an amount of 1 to 30 mass % as black iron oxide, based on an amount of the aqueous dispersion, and comprises 0.1 to 10 parts by mass of the hydroxypropylmethyl cellulose phthalate and 0.5 to 20 parts by mass of the alkyltriethoxysilane, relative to 100 parts by mass of the black iron oxide.

3. A method for preparing, a liquid cosmetic comprising an aqueous dispersion comprising a black iron oxide, water and hydroxypropylmethyl cellulose phthalate, wherein the method comprises a step of reacting a black iron oxide with alkyltriethoxysilane in water comprising hydroxypropylmethyl cellulose phthalate to obtain the aqueous dispersion of a black iron oxide surface-silylated with the alkyltriethoxysilane, wherein the black iron oxide is surface-silylated with an alkyltriethoxysilane and an amount of the aqueous dispersion in the liquid cosmetic is such that the amount of the black iron oxide is 0.1 to 40 mass %, relative to the liquid cosmetic.

4. The method according to claim 3, wherein the aqueous dispersion comprises the surface-silylated black iron oxide in an amount of 1 to 30 mass % as black iron oxide, relative to the aqueous dispersion, and comprises 0.1 to 10 parts by mass of the hydroxypropylmethyl cellulose phthalate and 0.5 to 20 parts by mass of the alkyltriethoxysilane, relative to 100 parts by mass of the black iron oxide.

5. The liquid cosmetic according to claim 1, having a viscosity at 25° C. of 1 to 300 mPa·s.

6. The liquid cosmetic according to claim 1, further comprising a film-forming polymer in an amount of 1 to 30 mass %, based on a total mass of the liquid cosmetic.

7. The liquid cosmetic according to claim 1, wherein the liquid cosmetic is an eyeliner.

8. The liquid cosmetic according to claim 2, having a viscosity at 25° C. of 1 to 300 mPa·s.

9. The liquid cosmetic according to claim 2, further comprising a film-forming polymer in an amount of 1 to 30 mass %, based on a total mass of the liquid cosmetic.

10. The liquid cosmetic according to claim 2, wherein the liquid cosmetic is an eyeliner.

11. The liquid cosmetic according to claim 5, wherein the liquid cosmetic is an eyeliner.

12. The liquid cosmetic according to claim 6, wherein the liquid cosmetic is an eyeliner.

13. The liquid cosmetic according to claim 7, wherein the eyeliner is placed in a pen-type container having a brush tip.

14. The liquid cosmetic according to claim 10, wherein the eyeliner is placed in a pen-type container having a brush tip.

15. The liquid cosmetic according to claim 11, wherein the eyeliner is placed in a pen-type container having a brush tip.

16. The liquid cosmetic according to claim 12, wherein the eyeliner is placed in a pen-type container having a brush tip.

* * * * *